United States Patent [19]

Wallace et al.

[11] Patent Number: 5,554,114
[45] Date of Patent: Sep. 10, 1996

[54] INFUSION DEVICE WITH PREFORMED SHAPE

[75] Inventors: George B. Wallace, Rancho Santa Margarita; Scott M. Evans, Santa Ana, both of Calif.; Andrew H. Cragg, Edina, Minn.

[73] Assignee: Micro Therapeutics, Inc., San Clemente, Calif.

[21] Appl. No.: 326,609

[22] Filed: Oct. 20, 1994

[51] Int. Cl.⁶ .................................................. A61M 25/00
[52] U.S. Cl. ............................. 604/53; 604/93; 604/280
[58] Field of Search .................... 604/271, 27, 28, 604/48, 52, 53, 93, 95, 264, 270, 280, 281, 282, 96, 194

[56] References Cited

U.S. PATENT DOCUMENTS

| | | |
|---|---|---|
| 3,890,977 | 6/1975 | Wilson . |
| 4,368,730 | 1/1983 | Sharrock . |
| 4,456,017 | 6/1984 | Miles . |
| 4,545,390 | 10/1985 | Leary . |
| 4,586,923 | 5/1986 | Gould et al. . |
| 4,619,274 | 10/1986 | Morrison . |
| 4,681,570 | 7/1987 | Dalton ............................ 604/281 X |
| 4,694,838 | 9/1987 | Wijayrathna et al. . |
| 4,724,846 | 2/1988 | Evans, III . |
| 4,738,667 | 4/1988 | Galloway ............................ 604/281 |
| 4,832,047 | 5/1989 | Sepetka et al. . |
| 4,955,862 | 9/1990 | Sepetka . |
| 5,025,799 | 6/1991 | Wilson . |
| 5,040,543 | 8/1991 | Badera et al. . |
| 5,078,684 | 1/1992 | Yasuda . |
| 5,085,635 | 2/1992 | Cragg . |
| 5,090,960 | 2/1992 | Don Michael . |
| 5,116,309 | 5/1992 | Coll ............................ 604/281 X |
| 5,122,136 | 6/1992 | Guglielmi et al. . |
| 5,178,158 | 1/1993 | de Toledo . |
| 5,184,627 | 2/1993 | de Toledo . |
| 5,209,727 | 5/1993 | Radisch, Jr. et al. . |
| 5,211,636 | 5/1993 | Mische . |
| 5,222,941 | 6/1993 | Don Michael . |
| 5,228,453 | 7/1993 | Sepetka et al. . |
| 5,295,962 | 3/1994 | Crocker et al. . |

FOREIGN PATENT DOCUMENTS

0486157A2  5/1992  European Pat. Off. .

*Primary Examiner*—Corrine M. McDermott
*Assistant Examiner*—N. Kent Gring
*Attorney, Agent, or Firm*—Joseph F. Breimayer

[57] ABSTRACT

An infusion guidewire or catheter for introduction through a selected path in a patient's vascular system to a site in a blood vessel and for infusing a drug or agent into the blood vessel. An elongated tubular body extends between a proximal and a distal end having an infusion device lumen formed therein extending to a plurality of infusion ports formed in a distal infusion segment of the elongated tubular body. The distal infusion segment is pre-biased to assume an infusion configuration when positioned in a blood vessel that tends to present the infusion port toward the blood vessel wall in a low blood flow rate zone and defining a generally centrally disposed perfusion lumen for perfusing blood therethrough. A core wire or a guidewire is inserted through said infusion device lumen from said proximal end into said distal infusion segment for changing the configuration to allow the advancement of the infusion device through the patient's vascular system to a desired site in a blood vessel and for allowing the distal infusion segment to assume said infusion configuration on withdrawal of the core wire or guidewire from the distal infusion segment.

25 Claims, 5 Drawing Sheets

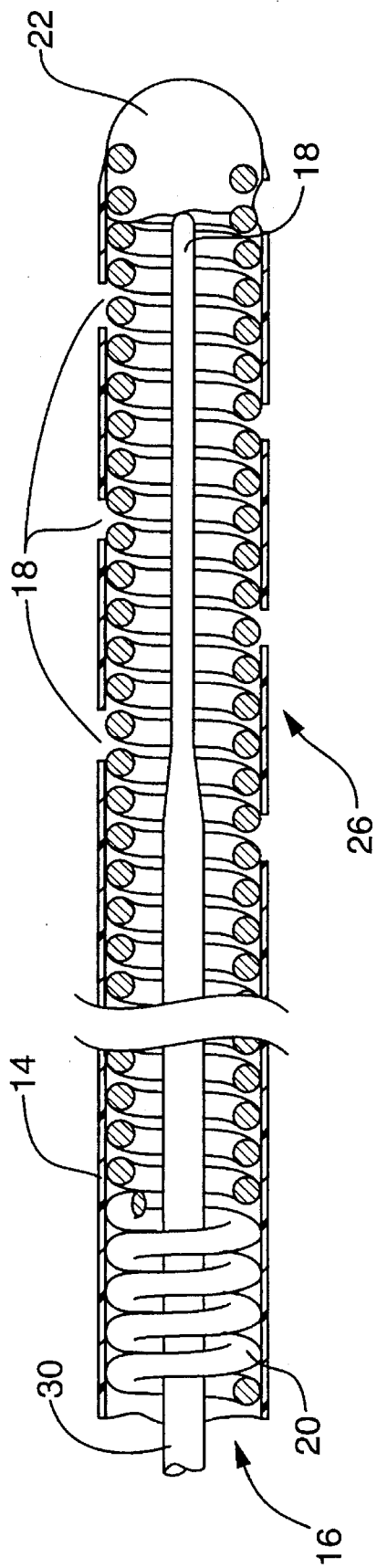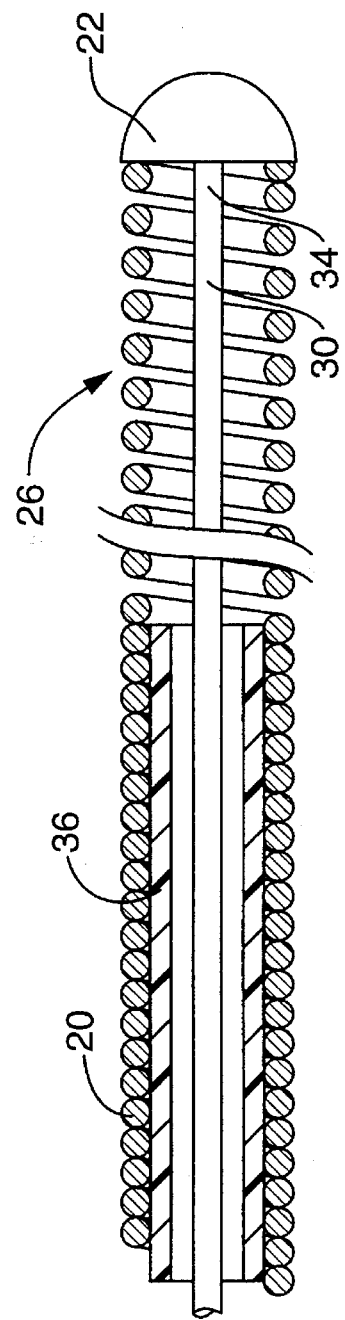
FIG. 2
FIG. 3

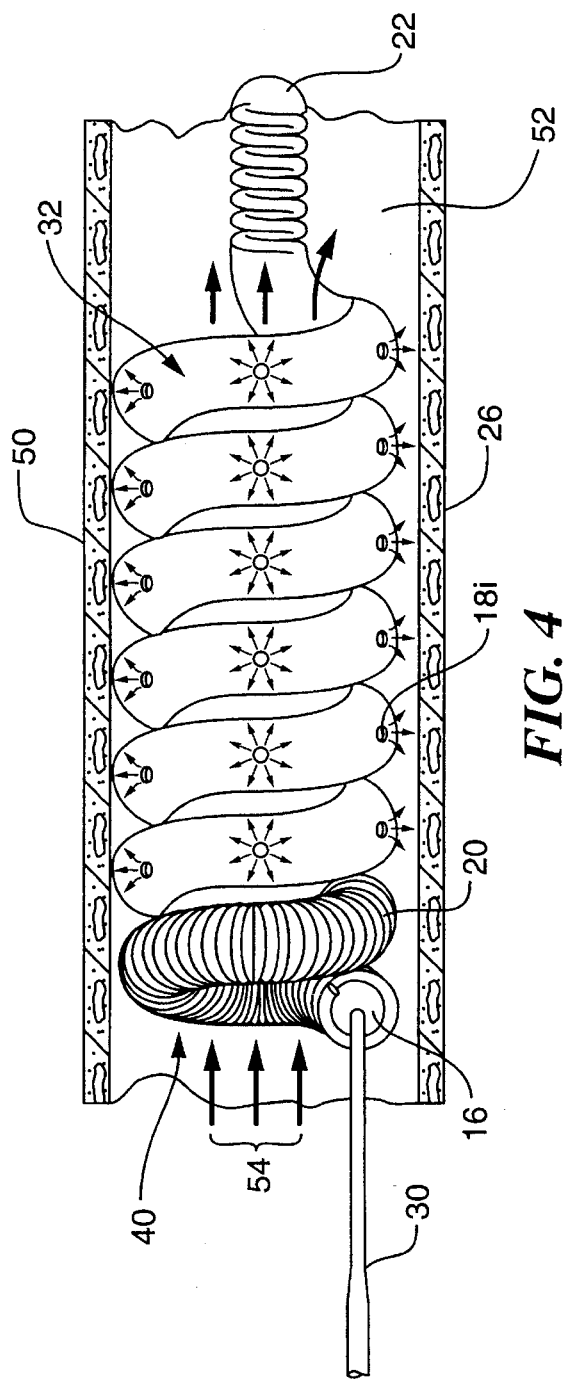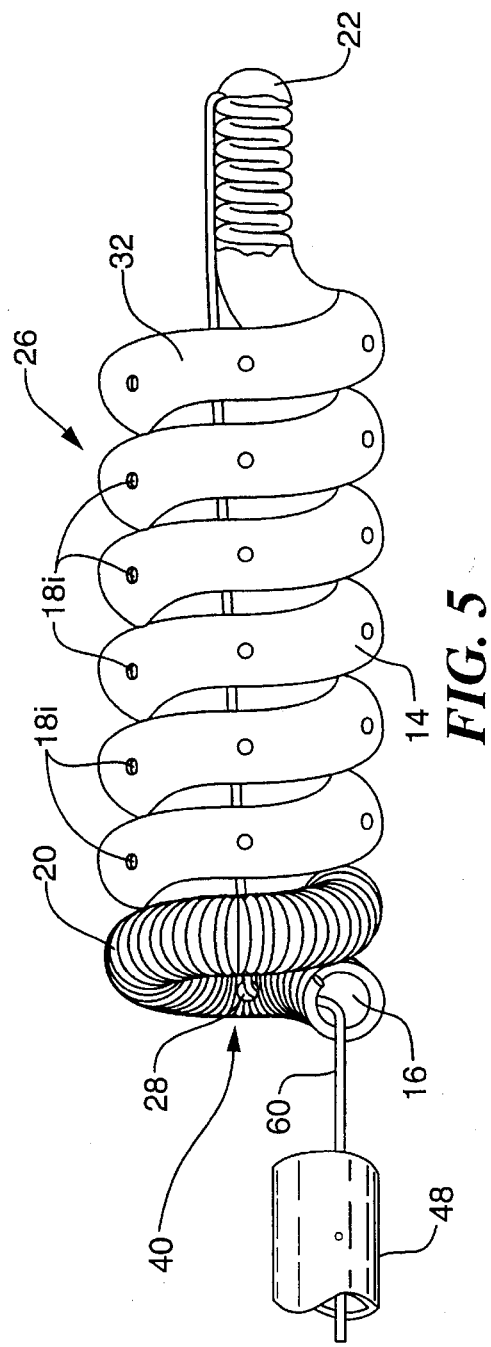

INFUSION DEVICE WITH PREFORMED SHAPE

BACKGROUND OF THE INVENTION

1. Field of the Invention

The present invention relates to medical devices, e.g. catheters or guidewires commonly used in the placement of catheters, particularly in a patient's vascular system, and particularly to convertible infusion wires that can be used either as a guidewire or a catheter, and, in either case, may be used for infusion of drugs or agents in close proximity with a blood vessel wall or other body cavity during the course of or following an interventional procedure.

2. Description of the Background Art

Medical catheters and guidewires are devices that can be navigated through narrow body passages, typically blood vessels, until the distal end section is in a desired location. Guide wires are typically used for introduction of a catheter over the guide wire. A physician controls the advancement and resulting position of the distal end of the guidewire by manipulations performed at the proximal end outside the body. Then the catheter is advanced over the guidewire, which may be left in place or withdrawn during a procedure using the guidewire.

Catheters generally comprise hollow, flexible tubes that convey fluids, such as contrast agents or pharmacological drugs to or from a desired blood vessel, organ or cavity through an internal catheter lumen. Cardiovascular balloon catheters have an inflatable balloon structure at the distal end for obstructing a blood vessel or, in the case of angioplasty, for expanding an occluded blood vessel.

Cardiovascular guidewires and catheters sometimes have similar structures, but guidewires typically have a solid core and are dimensioned to be received within a catheter lumen. One very common guidewire construction has an elongated, flexible, helical coil having a proximal end and a distal end, the latter being inserted into the patient's vascular system. An internal "core wire" typically extends through the coil lumen with the proximal and distal ends of the core wire attached to the proximal and distal ends of the coil.

In some helical coil guidewires used for cardiovascular purposes, the distal segment of the helical coil is J-shaped to provide improved steerability of the guidewire into various branches of a blood vessel, as shown, for example, in U.S. Pat. No. 5,040,543. A core wire that can be advanced into the coil lumen is provided to adjust the size of the J-shape curve in the distal segment by moving the core wire distally (to straighten out the J) or moving the core wire proximally (to reform the J). The ability to control the J-shape of the distal end increases the facility by which the guidewire can be manipulated to select a desired blood vessel at branch points.

In another application of a guidewire described in U.S. Pat. No. 5,122,136, a "guidewire" is constructed with a coil wire distal segment that may be advanced into an aneurysm and detached to effect thrombosis of the aneurysm cavity. The coil wire distal segment is itself pre-biased to assume a larger coil when released from a straight, surrounding micro-catheter lumen before it is inserted into the micro-catheter lumen and after it is introduced to the site of the aneurysm and advanced out of the lumen. In this configuration and use, the coiled wire distal segment does not function as a guidewire as otherwise described and referred to herein, since it can only be advanced to the site within the lumen of the micro-catheter.

Some guidewires, called "convertible wires" or "infusion guidewires" are constructed of coiled wire defining a guidewire lumen with an outer sheath surrounding or within the coiled wire and are adapted for use both as guidewires and as infusion catheters as disclosed, for example, in U.S. Pat. Nos. 5,178,158, 5,184,627 and 5,211,636. Such convertible wires may be provided with a fixed or removable core wire within the lumen to stiffen it during advancement.

Because of its narrow gauge, flexibility and column strength, the distal portion of a convertible wire can be advanced to a desired site in a blood vessel. Then the physician can advance a catheter over the convertible wire to the site. Depending on the design, the physician can remove the convertible wire from the catheter lumen or leave it in place while conducting a procedure with the catheter. Infusion of drugs or agents is typically effected from the proximal end, through the lumen and out through the distal end lumen opening or through side holes in the sheath or through the spaces between exposed turns of the coiled wire during or following the procedure using the catheter.

Such convertible wires are often employed in conjunction with procedures to temporarily open a blood vessel blockage in order to both provide the guidewire function to introduce a treatment catheter and to also provide infusion at the site of treatment either during or following the treatment.

The acute symptoms of blockage of a vein at a venous valve or a partially sclerosed and narrowed artery may be instigated by the presence of a soft obstruction or blood clot. In the venous and arterial blood vessels, such clots are referred to as an embolus or emboli and a thrombus or thrombi, respectively. Emboli and thrombi are characterized by a soft consistency that maintains a form and is resistant to dissolution in the bloodstream or in water and entraps red blood cells. Recently formed blood clots stabilized in position as emboli and thrombi are soft and jelly-like in consistency and are readily penetrated but reform after the penetrating object is removed. Such blood clots may form for a variety of reasons in the vascular system and be released and flow until they block a partially occluded section of the blood vessel. When this clot blocks a vessel in the leg, for example, the resultant pain or loss of circulation requires its removal or dissolution. When blocking cardiac arteries manifesting atherosclerosis, the resulting ischemic episode triggers the symptoms of chest pain or heart failure, with respect to cardiac arteries, or a stroke or eyesight failure, if the carotid artery or its tributaries are blocked. The invasive removal or dissolution of soft blood clots and the opening of hard obstructions in blood vessels have become commonplace.

To effect the initial opening of a soft obstruction, thrombolytic drugs or clot dissolving agents may be applied through an infusion catheter inserted into the clot to encourage the dissolution of the clot. For example, the infusion catheter disclosed in U.S. Pat. No. 5,085,635 is proposed to be introduced over a guidewire and be used for infusion of thrombolytic drugs (as well as diagnostic agents, in other procedures) out side wall openings into contact with the blood vessel wall. In many instances it may not be necessary to proceed further with a separate procedure to enlarge the blood vessel, if the soft obstruction can be dissolved in situ and the occlusion is not severe.

However, in the use of conventional infusion guidewires, convertible wires or catheters for introducing the dissolving agent, it is not always possible to maintain a concentration of the agent into the soft obstruction pressed against the blood vessel wall, where the infused agent would provide the most benefit. Laminar blood flow through the blood vessel washes the agent downstream before it may have the desired local effect.

Similarly, in other infusion applications following balloon angioplasty or other procedures affecting the blood vessel wall, the laminar blood flow through the vessel washes a drug or agent emitted radially for treatment of the vessel wall downstream before it may have the desired local effect.

In an approach to counter the loss of or more efficiently apply the drug or agent, specialized drug delivery dual balloon catheters have been developed to infuse drugs or agents against the vessel walls through holes in an outer balloon periphery or between two axially displaced, inflated balloons. The dual balloon catheters may have an inner through lumen for perfusion of blood while the balloons are in the inflated position for a matter of hours or days, as described, for example, in U.S. Pat. No. 5,295,962.

In the '635 patent, "pigtail" catheter designs of one or more loops having side wall openings are described, particularly in relation to rapid flush angiography for delivering contrast medium into a heart chamber. Such pigtail catheters are formed with the loop or loops formed in a planar configuration to minimize recoil of the catheter tip during the rapid and high pressure flush of the contrast medium into the heart chamber and blood vessels.

It would be desirable to provide local delivery of lytic agents to a blood clot to magnify their therapeutic effects while minimizing the complications of systemically delivered lytic agents e.g. bleeding. Similarly, it would be desirable to apply and concentrate agents at a blood vessel wall following an angioplasty dilation for treatment of the localized injury to the vessel. Despite the advances and improvements in treatment that have been introduced in recent years, a need remains for an infusion guidewire and catheter that provides a simple and less expensive way to assure delivery of drugs or agents in the low flow rate region adjacent to the blood vessel wall and/or obstructions while allowing perfusion of the blood through the generally central lumen of the blood vessel.

SUMMARY OF THE INVENTION

In view of the various and sometimes inconsistent uses of the terms in the background art, and in order to simplify the understanding of the invention, it is desirable to define the term "infusion device" used in the following description of the preferred embodiments and in the claims as applicable to and embracing infusion guidewires, convertible wires, infusion catheters and micro-catheters as described above, wherein the distal infusion segment thereof provides for infusion of a drug or agent in proximity to a vessel wall or in intimate contact with a soft obstruction in accordance with the present invention. The term "obstruction" is employed in the remaining description of the preferred embodiments and in the claims to embrace and be the equivalent of a "soft obstruction" comprising a blood clot or embolus or thrombus and a "hard obstruction" comprising an occlusion formed of atherosclerotic plaque on the vessel wall.

It is therefore a principal object of the present invention to provide an infusion device that makes intimate contact with and delivers drugs or agents for the dissolution of or otherwise treating a soft, recently formed obstruction in situ or contrast agent for radiologic identification of the soft obstruction.

It is a further principal object of the present invention to provide an infusion device that makes contact with a vessel wall and delivers drugs and agents at the vessel wall for treatment thereof.

It is a still further object of the present invention to provide such an infusion device having an infusion segment that expands to a preformed shape at the site of infusion for emitting the drug or agent in proximity to a vessel wall or within a soft obstruction of the vessel in the low blood flow rate region while allowing the laminar blood flow through the center of the vessel to continue.

It is yet another object of the present invention to provide for the extension of the expanded infusion segment through a length that encompasses the length of the soft obstruction or vessel wall to be treated from the proximal end of the infusion device.

These and other objects of the invention are realized in an infusion device for introduction through a selected path in a patient's vascular system to a site in a blood vessel and for infusing a drug or agent into the blood vessel comprising an elongated tubular body extending between a proximal and a distal end having a lumen formed therein extending from the proximal end to infusion ports formed in a distal infusion segment of the tubular body, the distal infusion segment formed to assume an infusion configuration when extended in a blood vessel that tends to present the infusion ports in a peripheral region of the blood vessel adjacent to the vessel wall in a low blood flow rate zone and defining a generally centrally disposed perfusion lumen for perfusing blood therethrough; and means for introducing said tubular body to allow its advancement through the patient's vascular system to a desired site in a blood vessel and for allowing the distal infusion segment to assume the infusion configuration on withdrawal of the introducing means from the distal infusion segment.

In a preferred embodiment of the invention, the introducing means comprises a core wire for insertion through the lumen from the proximal end into the distal infusion segment for changing the configuration to allow the advancement of the tubular body through the patient's vascular system to a desired site in a blood vessel and for allowing the distal infusion segment to assume the infusion configuration on withdrawal of the core wire from the lumen extending through the distal infusion segment. Alternatively, the introducing means may be an introducing catheter surrounding the infusion device during insertion that may be retracted proximally.

In the preferred embodiment, the configuration of the distal infusion segment is in the form of a loose helix that is assumed upon withdrawal of the introducing catheter or core wire. The formation of the loose helical configuration may be encouraged by drawing on the proximal end of a traction line extending from the proximal to the distal end of the infusion device to compress and expand the loose helix.

Moreover, the length of the expanded, loose helical distal infusion segment may be controlled by manipulation of the introducing means and/or the traction line so that it conforms to the length of a soft occlusion or vessel wall injury.

The present invention overcomes the problems associated with the prior art by providing an infusion device that may be dimensioned and otherwise constructed to have all of the advantages of a conventional infusion or convertible wire or infusion catheter wherein the drug or agent is infused in the low blood flow rate zone adjacent to the blood vessel wall or hard obstruction and in intimate contact within a soft obstruction while blood perfusion is allowed in the generally central high blood flow rate zone of the blood vessel. In the infusion or convertible wire embodiment, because the distal infusion segment can be straightened with the removable core wire and used as a guidewire, it can also be used for placement of other catheters, e.g. balloon catheters, pressure sensor, etc., by removing the standard fluid coupling from the proximal end and advancing the other catheter over the wire. The fluid coupling may be reattached and infusion of the drug or agent commenced upon withdrawal of the core wire and expansion of the turns of the distal infusion segment during or following the procedure employing the other catheter.

The present invention is therefore applicable either to convertible wires or to infusion catheters, where the core wire may in fact be a guidewire. Advantageously, the invention may be used in place of a separate, larger diameter infusion catheter or the double balloon catheters and reduce the expense attendant to the operative procedure.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 2 is a partially sectioned view of the distal end of the infusion device of FIG. 1 straightened for introduction through a blood vessel;

FIG. 3 is a partially sectioned view of the distal end of the infusion device in accordance with an alternative embodiment of the present invention straightened for introduction through a blood vessel;

FIG. 4 is a partially sectioned view of the distal end of the infusion device of FIG. 1 depicting its release into the expanded coil configuration upon retraction of a core wire;

FIG. 5 is a partially sectioned view of the distal end of the infusion device of FIG. 1 depicting an alternative manner of introducing the infusion device and drawing it into the expanded helical configuration of a preferred length;

The figures are not necessarily to scale.

DETAILED DESCRIPTION OF THE PREFERRED EMBODIMENTS

Figure 1:
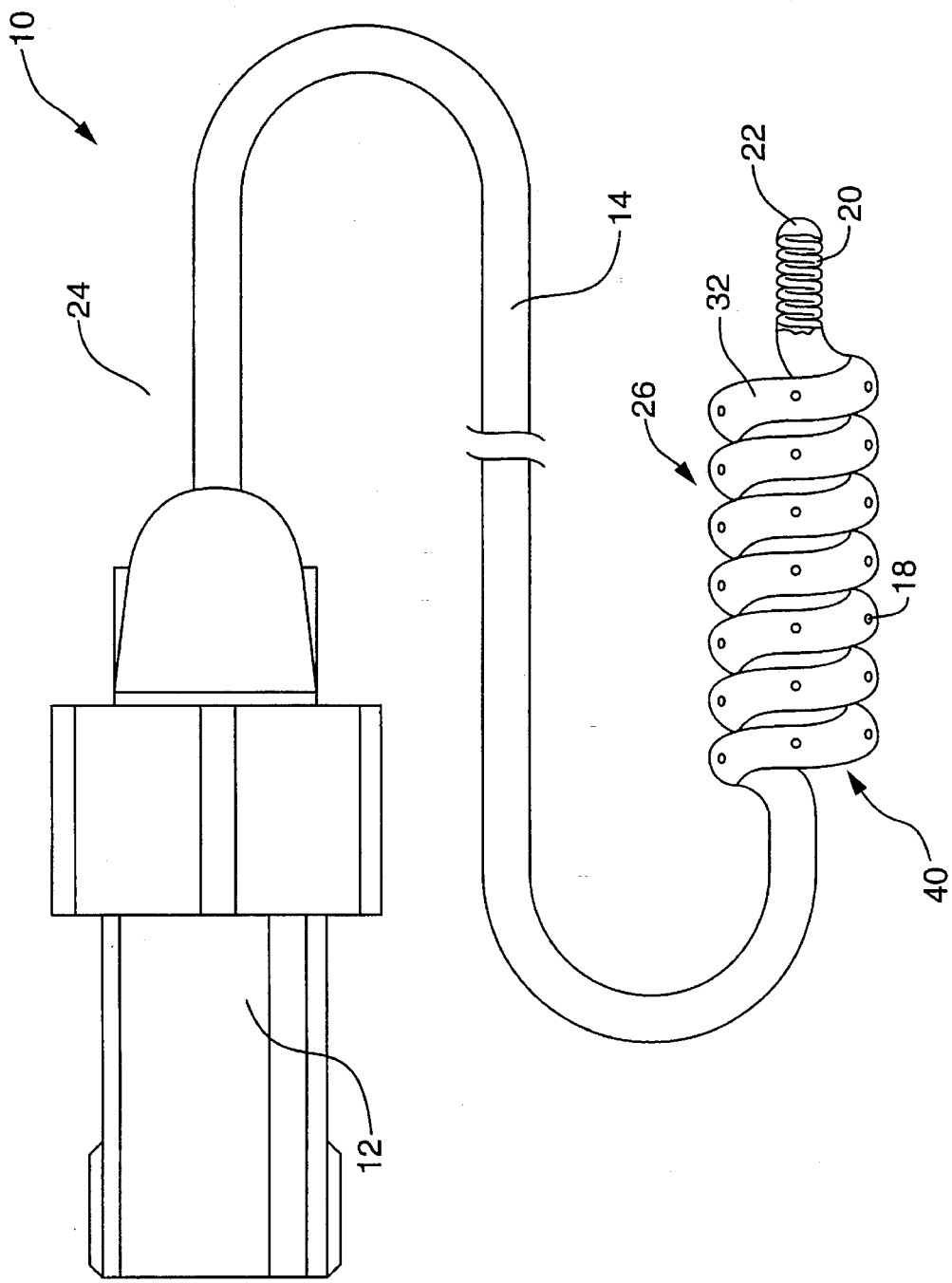
FIG. 1 is a conceptual view of an infusion device according to one embodiment of the present invention.

Turning first to FIGS. 1 and 2, they depict the construction of an infusion device 10 in accordance with one embodiment of the present invention in the relaxed, coiled, and in the straightened configurations of the distal infusion segment. The outer surface of the main body of infusion device 10 is a close or open wound, coiled wire 20 (as partially shown in FIG. 1 at the distal end thereof) covered by an outer sheath 14. A syringe or other pump system may be sealingly coupled to the proximal end of infusion device 10 by a standard Touhy-Borst connector 12 as shown in FIG. 1.

Introduction of the infusion fluid (a therapeutic drug or dissolving or contrast agent or the like) is preferably through the proximal opening of the coiled wire lumen within the connector 12. In the preferred mode, and not to be deemed as limiting of the invention, the infusion fluid is loaded into a syringe (not shown) in the normal fashion and is pressurized with manual force applied to the thumb knob attached to a piston (not shown) or into a pumping system. Touhy-Borst connector 12 can be removed from the proximal end 24 of the guidewire 10 to allow the infusion device 10 to function as an ordinary guidewire using a removable core wire 30 to facilitate placement of other catheters as described in the above-referenced '636 patent. A solid, radiopaque distal tip 22 is attached to the distal end of coiled wire 20 in the manner known in the art by welding, brazing, soldering, etc. The length of the straight section of the infusion device 10 between the distal end of the distal infusion segment 26 and the distal tip 22 may vary, depending on the application as either a convertible wire or strictly as an infusion catheter.

The pressurized infusion fluid is conveyed through the inner lumen 16 of infusion device 10 to be emitted from a series of n infusion ports $18_1$–$18_n$ in the outer sheath 14 in the distal infusion segment 26 when the core wire 30 is retracted therefrom. The distal infusion segment 26 may be formed into a loose, expanded helical coil configuration 32 by winding the coiled wire 20 about a mandrel before or after it is covered with sheath 14. The expanded helical configuration 32 defines a low tension spring of a number of spring coil turns surrounding a generally centrally disposed blood flow lumen 40 when it is not straightened by full insertion of the core wire 30. The infusion ports $18_1$–$18_n$ may be formed by slitting, puncturing or laser drilling the sheath 14 in the distal infusion segment 26. The infusion ports $18_1$–$18_n$ are then directed either toward the blood vessel wall or generally in the low blood flow peripheral region of the blood vessel when the distal infusion segment 26 is released and allowed (or encouraged as described below in reference to FIG. 5) to form the loose expanded helical configuration 32. A minority of the infusion ports $18_1$–$18_n$ may be aimed centrally, depending on their location and the shape of the helical turns. Alternatively, the infusion ports $18_1$–$18_n$ may be formed in the outer exposed periphery of the turns of the expanded helical configuration 32.

The coiled wire 20 terminates at the proximal end 24 within the Touhy-Borst connector 12 by a proximal lumen opening (not shown) for receiving the infusion fluid. The lumen opening also receives the removable core wire 30 (shown in FIGS. 2–4) which may be extended the length of the guidewire lumen 16 to contact the distal tip 22 and straighten out the distal infusion segment 26 as shown in a partially sectioned view of the first preferred embodiment of the present invention in FIG. 2.

As shown in FIG. 2, the interior lumen 16 of the infusion device 10 contains the solid, tapered core wire 30 terminating in a free end 34 bearing against the distal tip 22 so that the force applied from the proximal end straightens out the loose coil configuration 32. The handling characteristics of infusion device 10 may be improved by tapering solid core wire 30 beginning at a point proximal to the distal tip 34.

Although FIGS. 1 and 2 depict a series of infusion ports $18_1$–$18_n$ formed in the outer sheath 14, it will be understood that in a further alternative, the outer sheath 14 may be replaced by an inner sheath with the infusion ports $18_1$–$18_n$ formed therein. Or the sheath 14 may be a polymer coating filling the gaps between the turns of the coiled wire 20 with the infusion ports $18_1$–$18_n$ formed by openings in the coating between turns of the coiled wire 20 in the distal infusion segment.

Alternatively, the sheath 14 may be entirely removed along the distal infusion segment 26 so that the infused drug or agent may be allowed to escape through the gaps between the coiled wire turns forming infusion ports $18_1$–$18_n$. Turning to FIG. 3, it depicts a variation on this second embodiment of the invention wherein the outer sheath 14 is replaced by an inner sheath 36 terminating where the distal infusion segment 26 begins. The closely wound turns of the coiled wire 20 are somewhat expanded in the distal infusion segment 26 as depicted to form a spiral gap through the length of the distal infusion segment 26. It will be understood that the tight winding may be retained in the distal infusion segment 26 since the gap width may expand with the release and expansion of the distal segment 26 into the unrestrained, loose expanded helical configuration 32.

FIG. 4 is a partially sectioned view of the distal end of the infusion device of FIG. 1 depicting its release from the straightened position of FIG. 2 into an expanded spiral coil, infusion configuration 32 through the length of the distal infusion segment 26 and in relation to a blood vessel wall 50. The core wire 30 is shown after withdrawal from the coiled wire lumen 16 of the distal infusion segment 26. The expanded helical configuration 32 may have an outer coil diameter on the order of 3–4 times the outer diameter of the coiled wire 20, which itself may have an outer diameter on the order of 0.014–0.038 inches, and the helical turns may roughly expand to conform to the diameter of the blood vessel lumen 52. The spiral coil expansion into the helical infusion configuration 32 creates a blood perfusion lumen 40 inside the coil turns that is disposed centrally in a blood vessel to allow and direct the laminar flow of blood therethrough in the direction of arrows 54 (or the reverse direction).

At the same time, the orientation of the infusion ports $18_1$–$18_n$ formed in the outer sheath 14 circumferentially on the outside of the spiral coil infusion configuration 32 distributes the infused drug or agent into the vicinity of the interior wall of the blood vessel 50 or in the adjacent region. In this manner, the drug or agent is distributed into the low blood flow rate, boundary layer region and is kept there for a longer period to treat a damaged vessel wall either in a stand alone procedure or following an earlier procedure, e.g. an angioplasty or atherectomy procedure using a separate balloon catheter previously introduced over the straight infusion device 10.

The overall length and number of infusion coil turns formed in the loose, expanded helical configuration 32 of the distal infusion segment 26 may be varied by selectively retracting the core wire 30. Infusion fluid may be delivered through the lumen 16 with the core wire 30 in place in such selective partial retraction. The length of the expanded helical configuration 32 may be adjusted to fit the length of the obstruction or vessel wall into or toward which the infusion fluid is delivered.

FIG. 5 is a similar, partially sectioned view of the distal end of the infusion device of FIG. 1 depicting an alternative manner of introducing it and of drawing the distal infusion segment 26 into the expanded helical configuration of a preferred length. In this variation, an introducer catheter 48 is advanced to the site of treatment in the vascular system, and the infusion device 10 including the distal infusion segment 26 is then introduced down the lumen of the introducer catheter 48. Alternatively, both are introduced together to the treatment site. Any conventional introducer catheter 48 or sheath may be employed for the purpose of straightening and guiding the infusion device 10 to the desired position, in a manner well known in the art. The introducer catheter 48 may then be withdrawn as shown in FIG. 5 to allow the distal infusion segment 26 to assume its unrestrained expanded, loose helical configuration 32. As with use of the core wire 30, the partial withdrawal of the introducer catheter 32 may be used to adjust the overall length of the expanded, loose helical configuration 32 to match the length of a soft obstruction or vessel wall injury.

Figure 6:
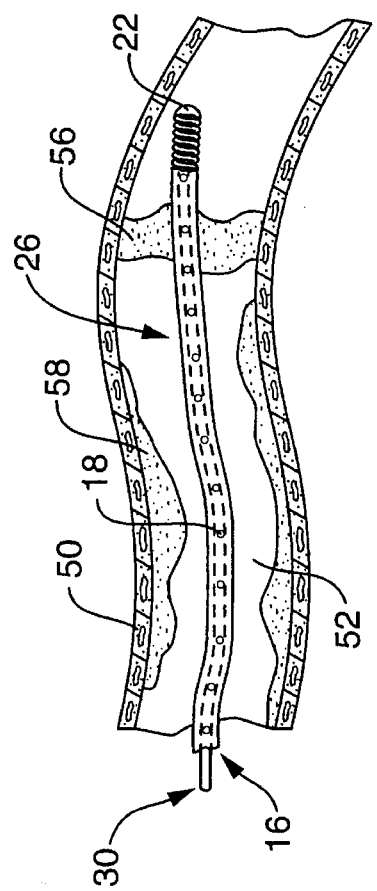
FIGS. 6–9 are views illustrating the method of introducing an infusion device, particularly a convertible wire, of the present invention into a soft obstruction and delivering drugs or agents into the obstruction and into proximity with the side wall of the blood vessel while allowing perfusion of blood centrally through the vessel.

In the further embodiment of the invention depicted in FIG. 5, a fine traction line 60 that may be used to aid in the formation of the helical configuration 32 and adjust its length. The traction line 60 extends the length of the coiled wire lumen from the proximal end 24 of the infusion device 10 and out one of the proximal infusion ports 18 or an especially positioned line exit port 28 and then alongside the outer sheath 14 and is attached to the distal tip 22 (or just past the distal turn of the expanded helical configuration 32). As shown in FIG. 6, the turns of the of the distal infusion segment 26 are pulled together tightly by tension applied to the traction line to draw the distal infusion segment 26 into the fully expanded helical configuration 32.

During introduction, the distal infusion segment 26 is straightened within the introducer catheter 48 (or by the core wire 30) as described above. Although not shown, it will be understood that when the distal infusion segment 26 is straightened, the traction line 60 may be spirally wound about the outer sheath 14 between the exit port 28 and the tip attachment point. Upon advancement out the introducer catheter lumen, the distal infusion segment 26 assumes the unrestrained expanded, loose helical configuration 32 described above. The traction line 60 may then be pulled upon from the proximal end to assist the formation of the expanded helical configuration 32 and to control its length and the spacing of adjacent turns by the application of compressive force that tightens the helical configuration 32. This assistance may be helpful even if the distal infusion segment has been preformed or pre-biased to assume the expanded helical shape of the infusion coil configuration 32 when unrestrained.

As shown in FIG. 5, the traction line 60 traverses alongside the helical configuration 32 and back into only the exit port 28. It will be understood that the traction line 60 may be inserted through several of the infusion ports $18_i$ aligned so that when tensile force is applied, the distal end 22 is pulled proximally, and the expanded helical configuration 32 is encouraged to form. It will also be understood that the traction line 60 may be threaded through one or more of the spacings between the exposed coiled wire turns in the embodiment of FIG. 3 to provide the compressive force when retracted, The infusion device 10 may be constructed by any of the known methods in monofilar and in multi-filar coiled wire windings and in one or more coaxial coils of circular or rectangular cross-section wire around an inner lumen 16 in a manner shown, for example, in the above-referenced '636, '627 and '158 patents. For simplicity of illustration, a monofilar, circular crosssection coiled wire 20 is depicted in the figures. In any of the depicted embodiments, coiled wire 20 is preferably a spring coil of stainless steel wire which is wound with a constant or variable pitch.

However, a memory metal, e.g a Ni-Ti alloy or other memory material, may also be used to form the loose expanded helical configuration 32 at a transition temperature that may, for example, be body temperature. In such a case, the elevation of the temperature of the distal infusion segment 26 from room to body temperature effects the change from straight to coiled configuration upon removal of the stiffening core wire 30. The temperature of the wire may also be elevated by the use of other energy sources such as by passing an electrical current through the wire. To return to the straight configuration of FIG. 2, it may be desirable to infuse a low temperature saline to cool the memory metal alloy below the transition temperature.

The outer and inner sheaths 14 and 36 are only illustrative of a variety of sheath configurations that may be employed, e.g. those disclosed in the abovereferenced '636, 627 and '158 patents. The sheaths 14 and 36 may be fabricated as tubes inserted over or within the lumen 16 of the coiled wire 20 or may be coatings or heat shrunk tubings applied to the coiled wire 20 in a manner well known in the art. Any of the well known materials used in fabrication of guidewires and catheters may be used for the thin, non-porous and high pressure sheaths 14 and 36, including polyethylenes, urethanes, silicone rubber or PTFE compounds, etc.

As indicated above, the present invention is also applicable to the design of infusion catheters or microcatheters having a somewhat larger overall diameter and often having a single lumen or multiple lumens for an inflatable balloon or sensor or other feature. Such catheters may or may not be reinforced with one or more coiled wires or hypo tubes as is well known in the art. Such catheters may be introduced into the vasculature by using an over-the-wire or monorail type insertion technique. For example, the single lumen infusion catheter disclosed in the above referenced '635 patent may be modified at the distal infusion segment in accordance with the present invention.

The single lumen infusion catheter of the '635 patent has a self-sealing distal end opening to the single lumen to allow advancement over a previously advanced guidewire. In such an application of the present invention to a larger diameter infusion catheter, the distal tip 22 depicted in the figures may be replaced by the self-sealing distal tip valve of the '635 patent to take advantage of the over the wire advancement.

Figure 7:
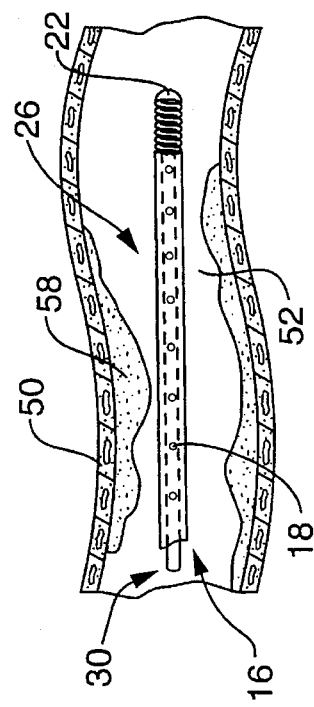

FIGS. 6–9 are views illustrating a method of introducing any one of the embodiments of the infusion device 10 of the present invention into a soft obstruction 56 and a hard obstruction 58 in the blood vessel 50 and delivering drugs or agents into the soft obstruction 56 and into proximity with the side wall of the blood vessel 50 while allowing perfusion of blood centrally through the coil lumen 40. In FIG. 6, the distal infusion segment 26 of the guide wire 10 is straightened and advanced with the core wire 30 in the coiled wire lumen 16 past a narrowing or partial occlusion on the walls of the blood vessel 50 and toward the soft obstruction 56. In FIG. 7, the distal tip 22 is passed through the soft obstruction 56 to position the distal infusion segment 26 midway through the obstruction 56. The positioning may be aided by use of conventional fluoroscopy and by tracking radiopaque markers formed in the guidewire 10 at the ends of the distal infusion segment 26 in a manner well known in the art.

Figure 8:
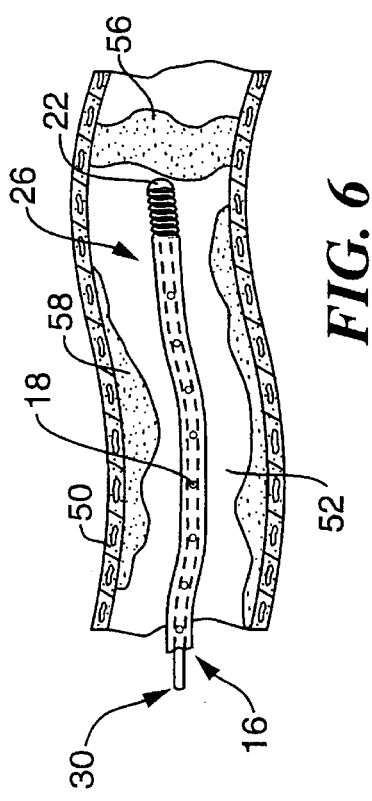
Figure 9:
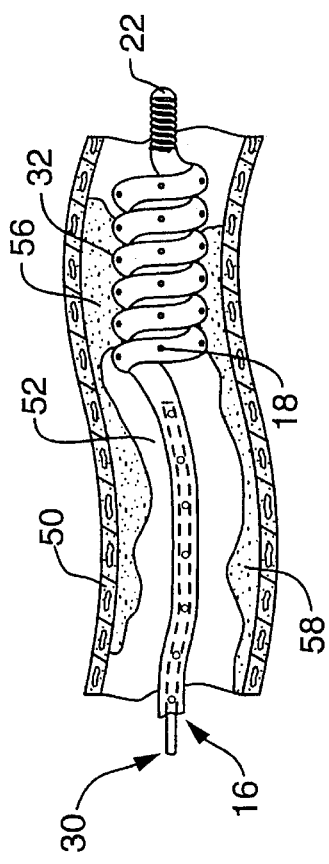
Figure 10:
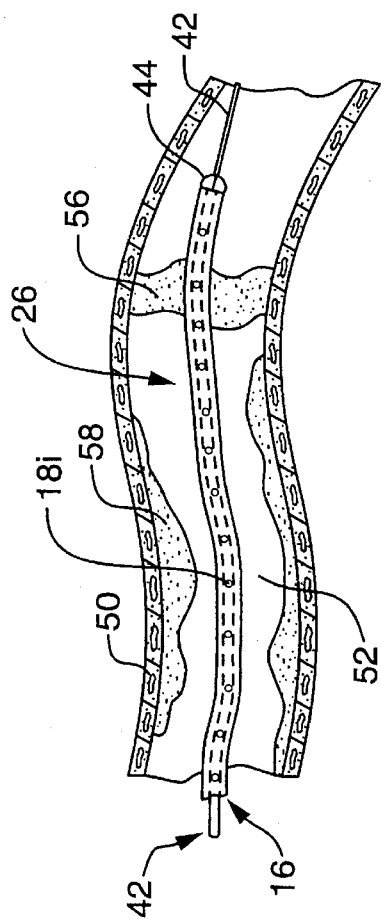
FIGS. 10–13 are views illustrating the method of introducing an infusion device, particularly an infusion catheter, of the present invention into a soft obstruction and delivering drugs or agents into the obstruction and into proximity with the side wall of the blood vessel while allowing perfusion of blood centrally through the vessel.

In FIG. 8, the core wire is retracted (and the line 60 is pulled, if present or the memory metal reacts to the body temperature, if used), and the helical configuration 32 is formed. The expansion of the infusion coil helix forces the coil turns into the soft obstruction, helping to press it toward the wall of the blood vessel 50 and to increase the surface area to be treated by the infused dissolving agent. Then, the dissolving agent may be infused into the pressed soft obstruction at a slow rate while the blood is allowed to flow through the infusion coil lumen 40 in the same manner as described above with respect to FIG. 4. The slow infusion of the dissolving agent into the obstruction and in the region of low blood flow rate, provides for a rapid dissolution, using minimal amounts of dissolving agent. After the obstruction 56 is dissolved, the core wire 30 is advanced to straighten the distal infusion segment 26 as shown in FIG. 9, and the infusion device 10 is then withdrawn.

FIGS. 10–13 depict the same steps of FIGS. 6–9 but using the infusion device of the present invention specifically as a single lumen infusion catheter 10 wherein the catheter is advanced over a guidewire 42 previously advanced through the obstructions 58 and 56. In this configuration, a distal end self sealing valve 44 is substituted for the solid distal tip 22, and the guide wire 42 penetrates the valve 44 during advancement of the infusion catheter 10. Such a self-sealing valve 44 with three flap leaflets is disclosed in the above-referenced '635 patent, incorporated by reference herein.

Figure 11:
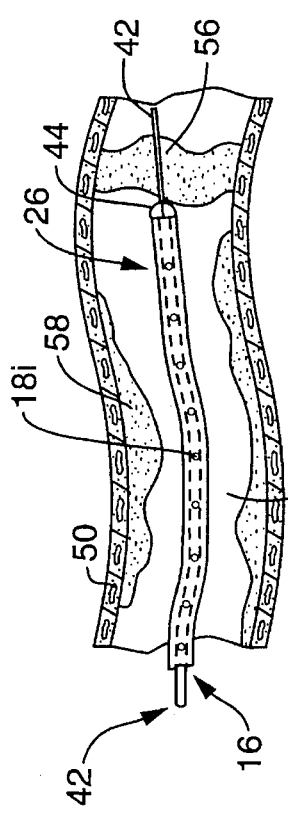
Figure 12:
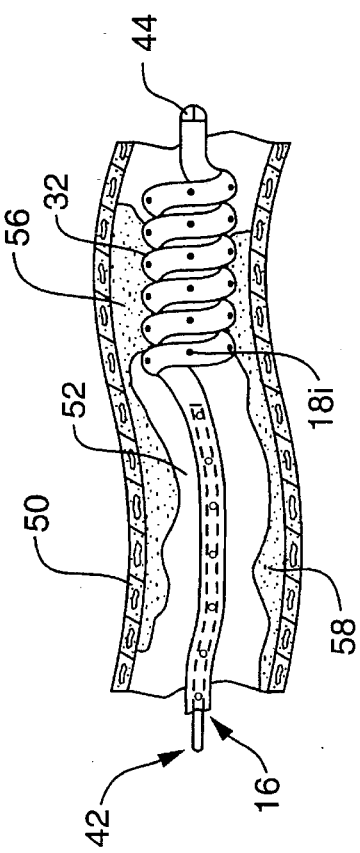
Figure 13:
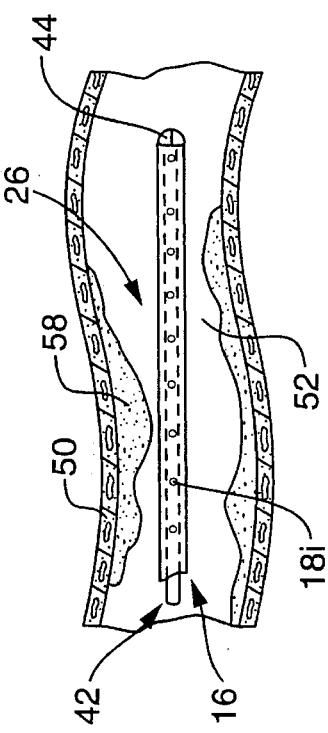

In FIG. 11, the distal end of the catheter is passed through the soft obstruction 56 to position the distal infusion segment 26 midway through the obstruction 56. The coil configuration 32 is formed by retraction of the guidewire 42 in FIG. 12 and actuation of the pull line 60, if present, or the operation of the memory metal in response to a change in temperature, if either are used. After the infusion is completed, the guidewire 42 is again advanced past the distal infusion segment 26 to straighten it, and the guidewire 42 and catheter body are withdrawn.

The same method steps may be employed to advance the distal infusion segment 26 into position with respect to a vessel wall injury. The method is especially applicable after a balloon angioplasty or atherectomy procedure has compressed or excised the hard obstruction but left the expanded or cleared vessel wall injured by the therapy. In this situation, it is often necessary to infuse drugs into the vessel wall to treat the injury response. The infusion device of the present invention may be dimensioned and configured as a convertible wire and used as the guide wire for the angioplasty or atherectomy catheter and then used in the manner described to infuse the drug.

In the case where the distal infusion segment is formed with a memory metal, e.g. a Ni-Ti alloy that assumes the helical configuration 32 at an elevated temperature, it will be understood that the method steps depicted in FIGS. 6–9 and 10–13 may include the further steps of infusing a cooling fluid, e.g. cooled saline, down the lumen 16 during introduction of the infusion device to keep the coiled wire 20 from assuming the helical configuration 32 until the position of FIGS. 7 and 11. Then, to return to the straight shape of FIGS. 9 and 13, it may be necessary to again inject a cooling fluid to aid in straightening the distal infusion segment 26 during withdrawal of the infusion device.

Although the preferred embodiments depict a single, distal, infusion segment 26, it will be understood that more than one such infusion segment as described above may be formed along the length of the infusion device body. Moreover, it will be understood that the distal infusion segment as described above in its various embodiments refers to any such infusion segment located anywhere along the length of the infusion device body distal to the proximal end thereof and not necessarily at the location generally depicted in the figures.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. A method for introducing a drug or agent into a desired infusion site in a blood vessel and for infusing a drug or agent into the blood vessel in the peripheral low blood flow rate region thereof comprising the steps of:

providing an infusion device having an elongated tubular body comprising a distal infusion segment and a proximal segment and a proximal and distal end and having an infusion lumen formed therein extending along the axis of the elongated tubular body from the proximal end to the distal infusion segment and a plurality of infusion ports comprising a first portion, a second portion add a third portion formed in, and distributed along the length and around the circumference of said distal infusion segment of the tubular body distal to a proximal segment of the tubular body;

forming said distal infusion segment of said elongated tubular body to assume an expanded helical coil infusion configuration of at least two turns extending axially and outwardly from the proximal segment when positioned at a desired infusion site in a blood vessel, the expanded helical coil infusion configuration providing a generally centrally disposed higher flow rate perfusion lumen for perfusing blood centrally therethrough and locating the plurality of infusion ports in the peripheral low blood flow rate region of the blood vessel, such that at least said first portion of the plurality of infusion ports face outward toward the vessel wall, said second portion of the plurality of infusion ports face axially toward adjacent turns of the expanded helical coil, and said third portion of the plurality of infusion ports face inward toward the perfusion lumen;

straightening the expanded helical coil infusion configuration of said distal infusion segment for facilitating advancement of said distal infusion segment to a selected location in a blood vessel;

advancing said infusion device with said straightened distal infusion segment through the patient's vascular system to located said distal infusion segment at a desired site in a blood vessel allowing said distal infusion segment to assume said expanded helical coil infusion configuration; and introducing an infusion fluid into the lumen for infusion through said plurality of infusion ports in the low blood flow rate region adjacent to said blood vessel wall.

2. The method of claim 1 wherein:

said straightening step further comprises inserting a core wire through said infusion device lumen from said proximal end into said distal infusion segment for straightening said expanded helical coil infusion configuration;

said advancing step further comprises advancing said infusion device with said core wire through the patient's vascular system to locate said distal infusion segment at a desired infusion site in a blood vessel; and said allowing step further comprises retracting said core wire from said distal infusion segment and allowing said distal infusion segment to assume said expanded helical coil infusion configuration.

3. The method of claim 2 further comprising the steps of:

advancing said core wire as a guide wire into said blood vessel to said selected location;

said restraining step further comprises advancing said infusion device over said guide wire to straighten said distal infusion segment; and said advancing step further comprises continuing to advance said infusion device over said guidewire through the patient's vascular system to locate said distal infusion segment at a desired site in a blood vessel.

4. The method of claim 1 further comprising the step of:

advancing an introducer catheter having a lumen dimensioned to receive said infusion device to straighten and restrain said distal infusion segment to a desired infusion site in a blood vessel; and wherein:

said straightening step further comprises advancing said distal infusion segment into said introducer catheter lumen;

said step of advancing said infusion device further comprises advancing said infusion device within said introducer catheter lumen through the patient's vascular system to locate said distal infusion segment at said desired infusion site in a blood vessel; and said allowing step further comprises retracting said introducer catheter from said distal infusion segment and allowing said distal infusion segment to assume said expanded helical coil infusion configuration.

5. The method of any of the claims 1–4 further comprising the step of:

applying tension to said distal infusion segment following release of said distal infusion segment to encourage the assumption of the expanded helical coil infusion configuration and to adjust the length of said distal infusion segment with respect to the blood vessel.

6. A thrombectomy method for treating a soft obstruction within a patient's vascular system comprising the steps of:

providing an infusion device having an elongated tubular body comprising a distal infusion segment and a proximal segment and a proximal and a distal end and having an infusion lumen formed therein extending along the axis of the elongated tubular body from the proximal end to said distal infusion segment, a plurality of distal infusion ports comprising a first portion, a second portion and third portion formed in, and distributed along the length and around the circumference of said distal infusion segment of the tubular body distal to said proximal segment of the tubular body;

forming said distal infusion segment of the elongated tubular body to assume an expanded helical coil infusion configuration of at least two turns extending axially and outwardly from the proximal segment when unrestrained and positioned at a desired infusion site in a blood vessel, the expanded helical coil infusion configuration providing a generally centrally disposed higher flow rate perfusion lumen for perfusing blood centrally therethrough and locating said plurality of infusion ports in the peripheral low blood flow rate region of the blood vessel, such that at least said first portion of the plurality of infusion ports face outward toward the vessel wall, said second portion of the plurality of infusion ports face axially toward adjacent turns of the expanded helical coil, and said third portion of said plurality of infusion ports face inward toward the perfusion lumen;

restraining said distal infusion segment for changing said expanded helical coil infusion configuration to allow advancement of said distal infusion segment through the patient's vascular system;

advancing said infusion device with said distal infusion segment restrained through the patient's vascular system to position said distal infusion segment through a soft obstruction in the blood vessel;

releasing the restraint and allowing said distal infusion segment to assume said expanded helical coil infusion configuration and to press into intimate contact with said soft obstruction and generally toward the blood vessel wall; and introducing a treatment agent into the lumen for infusion through said infusion port and into the soft obstruction adjacent to the blood vessel wall in the low blood flow rate region.

7. The method of claim 6 further comprising the step of:

applying tension to said distal infusion segment following release of said distal infusion segment to encourage the assumption of the expanded helical coil infusion configuration and to adjust the length of said distal infusion segment with respect to the soft obstruction in the blood vessel.

8. An infusion device for introduction through a selected path in a patient's body to a desired infusion site in a blood vessel and for infusing a drug or agent into the peripheral low blood flow rate region adjacent the blood vessel wall comprising:

an elongated tubular body comprising a distal infusion segment and a proximal segment and a proximal and distal end and having an infusion lumen formed therein extending from the proximal end to the distal infusion segment, a plurality of infusion ports comprising a first portion, a second portion and a third portion formed in and distributed along the length and around the circumference of said distal infusion segment of the tubular body distal to a proximal segment of the tubular body in fluid communication with the infusion lumen;

means for forming the distal infusion segment to assume an expanded helical coil infusion configuration of at least two turns extending axially and outwardly from the proximal segment when positioned at a desired infusion site in a blood vessel, the expanded helical coil infusion configuration providing a generally centrally disposed nigher flow rate perfusion lumen for perfusing blood centrally therethrough and locating the plurality of infusion ports in the peripheral low blood flow rate region of the blood vessel, such that at least said first portion of the plurality of infusion ports face outward toward the vessel wall, said second portion of the plurality of infusion ports face axially toward adjacent turns of the expanded helical coil, and said third portion of the plurality of infusion ports face inward toward the perfusion lumen; and introducing means adapted to be advanced and withdrawn with respect to said distal infusion segment for altering said expanded helical coil infusion configuration of said distal infusion segment to allow its advancement through the patient's vascular system to the desired infusion site in a blood vessel when advanced with respect to said distal infusion segment and for allowing the distal infusion segment to assume said infusion configuration when withdrawn of said introducing means from the distal infusion segment.

9. The infusion device of claim 8 wherein said distal infusion segment of said elongated tubular body further comprises:

an elongated coiled wire surrounding said infusion lumen;

an elongated sheath enclosing said elongated coiled wire for sealing said infusion lumen; and wherein:

said plurality of infusion ports are formed as a plurality of openings in said sheath in said distal infusion segment for allowing passage of said infusion fluid therethrough and into the low blood flow rate region of a blood vessel adjacent to the blood vessel wall.

10. The infusion device of claim 9 wherein said elongated coiled wire and sheath are pre-biased to form said expanded helical coil infusion configuration in said distal infusion segment when said introducing means is withdrawn from said distal infusion segment.

11. The infusion device of claim 8 wherein said elongated tubular body further comprises:

an elongated, coiled wire extending from said proximal to said distal end and surrounding said infusion lumen;

an elongated sheath enclosing said elongated coiled wire extending from said proximal end to said distal infusion segment for sealing said infusion lumen to said distal infusion segment; and wherein:

said plurality of infusion ports are formed as the separations between adjacent turns of said elongated coiled wire extending through said distal infusion segment for allowing passage of said infusion fluid therethrough.

12. The infusion device of claim 8 wherein said elongated tubular body further comprises:

an elongated coiled wire extending from said proximal to said distal end and surrounding said infusion lumen, said elongated coiled wire pre-biased to form said helical coil infusion configuration in said distal infusion segment when said introducing means is withdrawn from said distal infusion segment.

13. The infusion device of claim 12 wherein said elongated tubular body further comprises:

an elongated traction line attached to said elongated coiled wire distally to said distal infusion segment and operable from the proximal end of said elongated tubular body to apply tension along said distal infusion segment to urge the formation of said expanded helical coil infusion configuration upon withdrawal of said introducing means from said distal infusion segment and to adjust the length of the helical coil infusion configuration.

14. The infusion device of claim 8 wherein said elongated tubular body further comprises:

an elongated coiled wire surrounding said infusion lumen in said distal infusion segment constructed of a temperature dependent memory material for assuming an expanded helical coil configuration when said introducing means is withdrawn from said distal infusion segment and when exposed to a temperature change at a desired infusion site in a blood vessel to provide said centrally disposed blood perfusion lumen.

15. The infusion device of claim 8 wherein said elongated tubular body further comprises:

an elongated traction line attached to said elongated tubular body distally to said distal infusion segment and operable from the proximal end of said elongated tubular body to apply tension to said distal infusion segment to urge the formation of said infusion configuration upon retraction of said core wire.

16. The infusion device of claim 8 wherein said introducing means further comprises:

a core wire for insertion through said infusion device lumen from said proximal end into said distal infusion segment for changing said infusion configuration to allow the advancement of said infusion device body through the patient's vascular system to a desired site in a blood vessel and for allowing said distal infusion segment to assume said infusion configuration on withdrawal of said core wire from said distal infusion segment.

17. The infusion device of claim 8 wherein said introducing means further comprises:

an introducer catheter having a lumen dimensioned to receive said elongated infusion body including said distal infusion segment for changing said infusion configuration to allow the advancement of said infusion device body through the patient's vascular system to a desired site in a blood vessel and for allowing said distal infusion segment to assume said infusion configuration on relative displacement of said introducer catheter core wire from said distal infusion segment.

18. The infusion device of any of the claims 8, 9,11, 12, 14 or 15 wherein:

said infusion device is formed as an infusion guidewire adapted to be introduced by said introducing means into a selected site in a blood vessel; and said introducing means is an elongated removable core wire for insertion through said infusion lumen from said proximal end into said distal infusion segment for changing said expanded helical coil infusion configuration to allow the advancement of said infusion guidewire through the patient's vascular system to a desired site in a blood vessel, allowing said guidewire to be used to guide introduction of catheter devices over the guidewire, and allowing said distal infusion segment to assume said infusion configuration on removal of said catheter device and withdrawal of said core wire from said distal infusion segment.

19. The infusion device of claim 8 wherein:

said infusion device is formed as an infusion catheter adapted to be introduced by said introducing means into a desired infusion site in a blood vessel; and said introducing means is an elongated removable guidewire for insertion through said infusion lumen from said proximal end into said distal infusion segment for changing said infusion configuration to allow the advancement of said infusion catheter through the patient's vascular system to a desired site in a blood vessel, and allowing said distal infusion segment to assume said infusion configuration on withdrawal of said guidewire from said distal infusion segment.

20. An infusion catheter for introduction through a selected path in a patient's body to a desired infusion site in a blood vessel and for infusing a drug or agent into the blood vessel in the peripheral low blood flow rate region thereof comprising:

an elongated catheter body comprising a distal infusion segment and a proximal segment and a proximal and distal end and having an infusion lumen formed therein extending from the proximal end the distal end infusion segment, and to a plurality of infusion ports comprising a first portion, a second portion and a third portion formed in a distal infusion segment of the catheter body distal to said proximal segment of the catheter body and adjacent to the distal end in fluid communication with the infusion lumen;

means for forming said distal infusion segment to assume an expanded helical coil infusion configuration of at least two turns extending axially and outwardly from the proximal infusion segment when positioned at a desired infusion site in a blood vessel, the expanded helical coil infusion configuration providing a generally centrally disposed higher flow rate perfusion lumen for perfusing blood centrally therethrough and locating the plurality of infusion ports in the peripheral low flow rate region of the blood vessel, such that at least said first portion of the plurality of infusion ports face outward toward the vessel wall, said second portion of the plurality of infusion ports face axially toward adjacent turns of the expanded helical coil, and said third portion of the plurality of infusion ports face inward toward the perfusion lumen;

a penetrable, self-sealing valve formed in said distal end of said elongated catheter body;

an elongated guidewire dimensioned to fit within said catheter lumen and extend through said self-sealing valve, whereby said guidewire straightens said expanded helical coil infusion configuration to allow the advancement of said infusion device body through the patient's vascular system over the guidewire to a desired infusion site in a blood vessel and said distal infusion segment is allowed to assume said expanded helical coil infusion configuration on withdrawal of said guidewire through said self-sealing valve and from said distal infusion segment.

21. The infusion catheter of claim 20 wherein said elongated catheter body further comprises:

an elongated coiled wire extending from said proximal to said distal end and surrounding said infusion lumen, said elongated coiled wire pre-biased to form said helical coil infusion configuration in said distal infusion segment when said introducing means is withdrawn from said distal infusion segment.

22. The infusion catheter of claim 21 wherein said elongated catheter body further comprises:

an elongated traction line attached to said elongated coiled wire distally to said distal infusion segment and operable from the proximal end of said elongated tubular body to apply tension along said distal infusion segment to urge the formation of said expanded helical coil infusion configuration upon withdrawal of said introducing means from said distal infusion segment and to adjust the length of the helical coil infusion configuration.

23. The infusion catheter of claim 20 wherein said elongated catheter body further comprises:

an elongated coiled wire surrounding said infusion lumen in said distal infusion segment constructed of a temperature dependent memory material for assuming an expanded helical coil configuration when said introducing means is withdrawn from said distal infusion segment and when exposed to a temperature change at a desired infusion site in a blood vessel to provide said centrally disposed blood perfusion lumen.

24. The infusion catheter of claim 20 wherein said elongated catheter body further comprises:

an elongated traction line attached to said elongated catheter body distally to said distal infusion segment and operable from the proximal end of said elongated catheter body to apply tension to said distal infusion segment to urge the formation of said infusion configuration upon retraction of said core wire.

25. The infusion catheter of claim 20 wherein said distal infusion segment of said elongated tubular body further comprises:

an elongated coiled wire surrounding said infusion lumen;
an elongated sheath enclosing said elongated coiled wire for sealing said infusion lumen; and wherein:
said plurality of infusion ports are formed as openings in said sheath in said distal infusion segment for allowing passage of said infusion fluid therethrough and into the low blood flow rate region of a blood vessel adjacent to the blood vessel wall.

* * * * *